US00PP18486P2

(12) United States Plant Patent
Smith

(10) Patent No.: US PP18,486 P2
(45) Date of Patent: Feb. 12, 2008

(54) ***LIBERTIA* PLANT NAMED 'TAUPO BLAZE'**

(50) Latin Name: *Libertia*
Varietal Denomination: TAUPO BLAZE

(76) Inventor: Phillip Smith, 155 Centennial Dr., Taupo (NZ)

( * ) Notice: Subject to any disclaimer, the term of this patent is extended or adjusted under 35 U.S.C. 154(b) by 135 days.

(21) Appl. No.: 11/441,725

(22) Filed: May 25, 2006

(51) Int. Cl.
*A01H 5/00* (2006.01)

(52) U.S. Cl. ..... Plt./384

(58) Field of Classification Search ..... Plt./384
See application file for complete search history.

*Primary Examiner*—Kent Bell
*Assistant Examiner*—Annette H Para

(57) ABSTRACT

A new cultivar of *Libertia* named 'TAUPO BLAZE' that is characterized by compact clumping habit, white star-like flowers, and pronounced burnt-red to scarlet foliage color in fall and winter. In combination these traits set 'TAUPO BLAZE' apart from all other existing varieties of *Libertia* known to the inventor.

2 Drawing Sheets

Genus: *Libertia* species: *ixioides*.
Denomination: 'TAUPO BLAZE'.

BACKGROUND OF THE INVENTION

The present invention relates to a new and distinct cultivar of New Zealand iris grown for use as an ornamental plant for container, border, and patio. The new cultivar is known botanically as *Libertia ixioides* and will hereinafter be referred to by the cultivar name 'TAUPO BLAZE'.

'TAUPO BLAZE' was discovered by the inventor at the inventor's nursery in Whenuapai, Auckland, New Zealand in 2002. The new *Libertia* variety 'TAUPO BLAZE' was discovered as a naturally occurring seedling selection within a commercially grown crop of *Libertia* 'Taupo Sunset' (unpatented). Selection was based on the criterion of pronounced burnt-red to scarlet foliage in fall and winter. The female parent is an individual, *Libertia ixioides* 'Taupo Senset' and the male parent is an individual *Libertia ixioides,* 'Taupo Sunset'. The closet comparison plant is 'Taupo Sunset' which exhibits foliage that is orange-yellow in color in fall and winter. 'TAUPO BLAZE' is distinguishable from the comparison plant by the pronounced burnt-red to scarlet foliage color in fall and winter.

'TAUPO BLAZE' is hardy and exhibits compact clumping habit, profusions of pure white star-like flowers from mid-spring to summer, stiff sword-shaped leaves that are green in spring, changing to strong orange-yellow in summer, then pronounced burnt-red to scarlet in fall and winter. In autumn the flowers give way to yellow berries. Asexual propagation is accomplished by the methods of tissue culture and division. Cultural requirements are moist, fertile soil, full sun to light shade and adequate but not excess water. Mature height and breadth is 0.6 m. 'TAUPO BLAZE' is hardy to USDA Zone 7.

'TAUPO BLAZE' was first asexually propagated in 2004 in Auckland, New Zealand. Asexual propagation was conducted by the inventor and the method utilized was tissue culture. Since that time under careful observation 'TAUPO BLAZE' has been determined stable, uniform, and reproduces true to type successive generations of asexual propagation.

SUMMARY OF THE INVENTION

The following traits have been repeatedly observed and represent the distinguishing characteristics of the new *Libertia* variety known as 'TAUPO BLAZE'. These traits in combination distinguish 'TAUPO BLAZE' from all other existing varieties of *Libertia* known to the inventor. 'TAUPO BLAZE' has not been tested under all possible conditions and phenotypic differences may be observed with variations in environmental, climatic, and cultural conditions. However, without any variance in genotype. Growing requirements are similar to the species.

1. 'TAUPO BLAZE' exhibits compact clumping habit.
2. 'TAUPO BLAZE' exhibits green foliage color in spring, changing to strong orange and yellow in summer, then pronounced burnt-red to scarlet in fall and winter.
3. 'TAUPO BLAZE' exhibits stiff erect sword-like leaves.
4. 'TAUPO BLAZE' is grown as an ornamental plant for container border, and patio.
5. 'TAUPO BLAZE' exhibits clusters of white star-like flowers from mid-spring, to summer followed by yellow berries in fall.
6. Cultural requirements for 'TAUPO BLAZE' include adequate but not excess water, moist fertile soil, and full sun to light shade.
7. 'TAUPO BLAZE' is propagated by the methods of tissue culture and division.
8. At maturity 'TAUPO BLAZE' reaches 0.6 m. in height and breath.
10. 'TAUPO BLAZE' is hardy to USDA Zone 7.

BRIEF DESCRIPTION OF THE DRAWING

The accompanying color drawings illustrate the overall appearance of the new *Libertia* variety named 'TAUPO BLAZE' showing colors as true as it is reasonably possible to obtain in colored reproductions of this type. The drawing labeled

BOTANICAL DESCRIPTION OF THE PLANT

Figure 1:
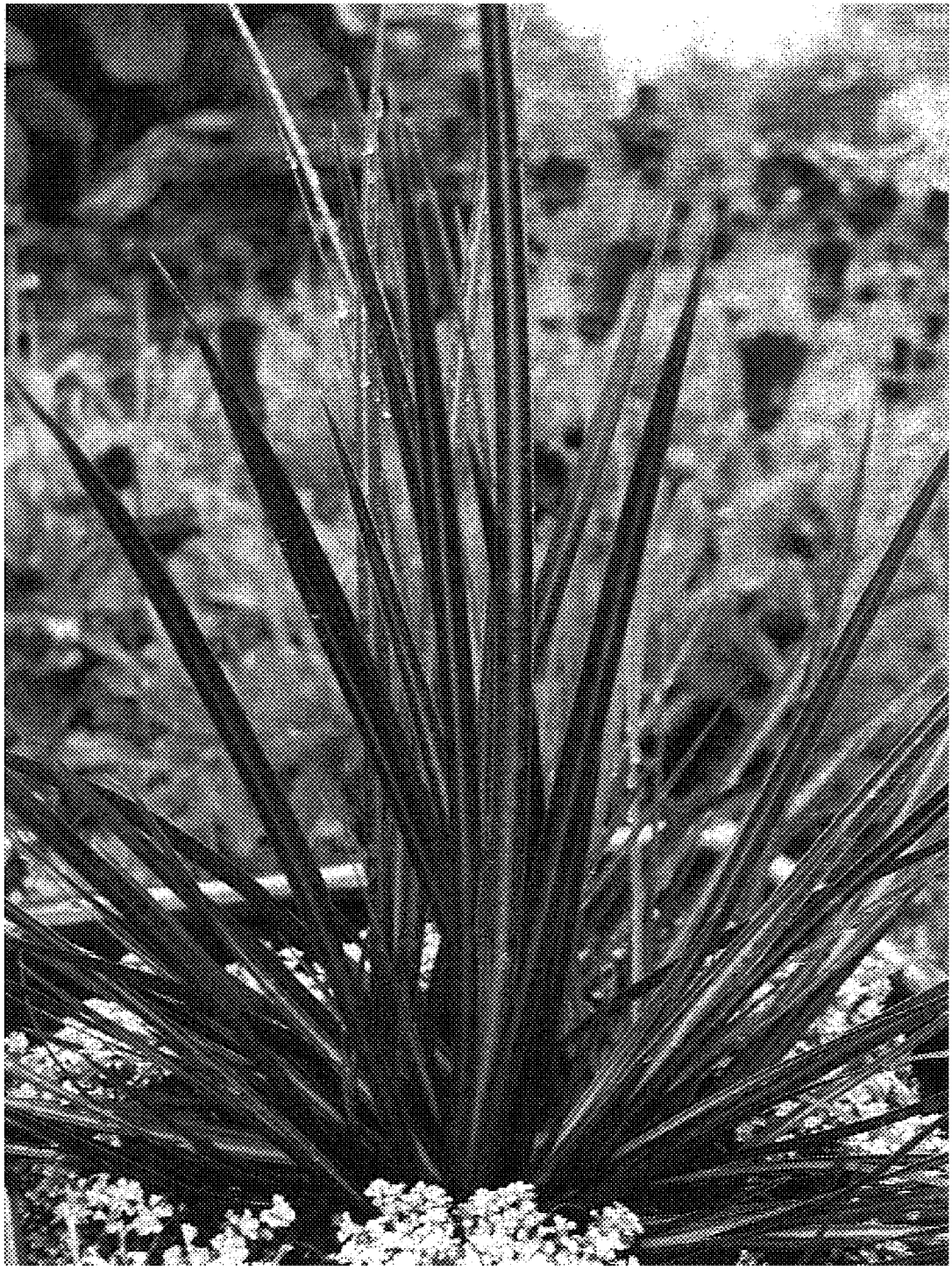
FIG. 1 depicts a hole plant from a side perspective illustrating habit of an 18 month old in a 2 liter pot grown out of doors in Auckland, NZ autumn. The drawing labeled
Figure 2:
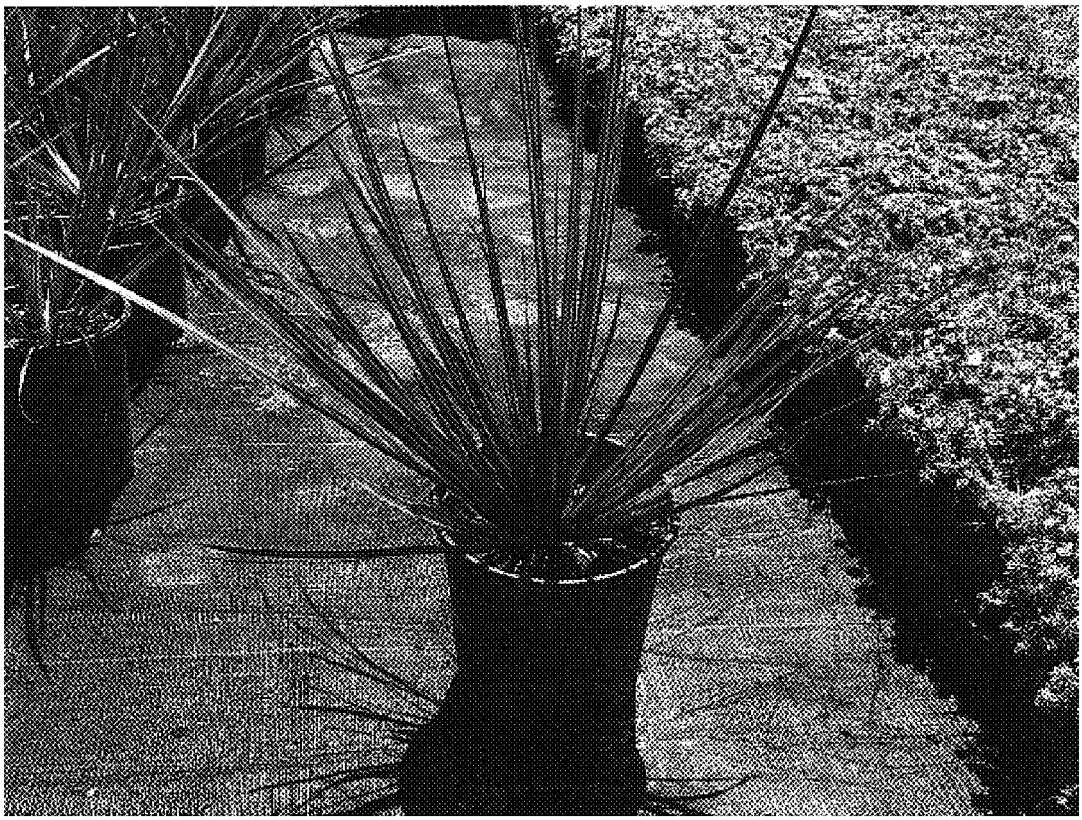
FIG. 2 depicts a whole plant from the side perspective illustrating habit of an 18 month old grown in Watsonville, Calif., in the spring. The color in the drawings may differ from color values cited in the detailed botanical description, which accurately describe the actual color of the new variety 'TAUPO BLAZE'. The drawings labeled FIG. 1 and FIG. 2 were made using conventional techniques and although flower and foliage color may appear different from actual color due to light reflectance, they are as accurate as possible by conventional photography.

The following is a detailed description of the new *Libertia* cultivar named 'TAUPO BLAZE'. Data was collected and compiled in winter 2005 and spring 2006 in a cultivated area of Arroyo Grande, Calif. from 18 month old 1-liter container plants. Color determinations are in accordance with the 2001 Royal Horticultural Society Colour Chart of London, England except where general color terms of ordinary dictionary significance are used. The growing requirements are similar to the species.

Botanical classification: *Libertia ixioides* 'TAUPO BLAZE'.
Family: Iridaceae.
Plant genus: *Libertia.*
Plant species: *ixioides.*
Plant denomination: 'TAUPO BLAZE'.
Common name: New Zealand iris.
Plant use: Grown as an ornamental plant for container, border, and patio.
Plant type: Perennial.
Parentage: The new cultivar *Libertia ixioides* 'TAUPO BLAZE' was discovered as a naturally occurring seedling within a growing crop of the following parents:
- *Female parent plant.*—An individual *Libertia* 'Taupo Sunset'.
- *Male parent plant.*—An individual *Libertia* 'Taupo Senset'.

Plant vigorous: Moderate.
Plant habit: Compact clumping habit.
Plant dimensions (first season): 0.3 m. in height and breadth.
Plant dimensions (at maturity): 0.6 m. in height and breadth.
Plant hardiness: Hardy to USDA Zone 7.
Plant propagation: Asexual propagation is achieved by the methods of tissue culture and division.
Plant root system.: Fibrous.
Plant cultural requirements: Cultural requirements include adequate but not excess water, moist fertile soil, and full sun to partial shade.
Pest susceptibility or resistance: Older plants are susceptible to mealy bugs.
Disease susceptibility or resistance: None known to the inventor.
Time to produce liner: 8–12 weeks from tissue culture to a 5 cm. liner pot.
Plant crop time: 16–24 weeks from tissue culture to a finished 20 cm. container.
Seasonal interest: Flowers, foliage color, berries.
Blooming season: Mid-spring to summer.

Foliage:
- *Foliage type.*—Evergreen.
- *Leaf quantity.*—Average of 110 leaves on a 2-liter container plant
- *Leaf shape.*—Gladiate.
- *Leaf texture.*—Stiff.
- *Leaf arrangement.*—Basal.
- *Branching.*—Erect.
- *Leaf apex.*—Slightly hooked.
- *Leaf base.*—Truncate.
- *Leaf division.*—Simple.
- *Leaf margin.*—Entire.
- *Stipules.*—None observed.
- *Spring leaf color* (*adaxial and abaxial surfaces*).—139A, 139C, N186B, 200C.
- *Summer leaf color* (*adaxial and abaxial surfaces*).—N167A and 167A.
- *Fall and winter leaf color* (*adaxial and abaxial surfaces*).—169A, 183A, 183D.
- *Leaf surface* (*adaxial and abaxial surfaces*).—Glabrous.
- *Leaf venation pattern.*—Parallel veins.
- *Leaf vein color* (*adaxial and abaxial surfaces*).—N167A, 143C, 167A.
- *Leaf length.*—Average is 49 cm.
- *Leaf width.*—Average is 0.60 cm.
- *Leaf fragrance.*—None observed.

Inflorescence:
- *Blooming months.*—Late April to mid-July.
- *Inflorescence type.*—Terminal panicle.
- *Flower quantity.*—Average of 16 flowers per inflorescence.
- *Persistent or self-cleaning.*—Self-cleaning.
- *Flower aspect.*—Facing upward.
- *Flower shape.*—Stellular.
- *Flower depth.*—1 cm.
- *Flower diameter.*—2 cm.
- *Corolla tube depth.*—7 mm.
- *Petals.*—3 in number.
- *Petal dimensions.*—0.90 cm. in length and 0.60 cm. in width.
- *Petals fused or unfused.*—Unfused.
- *Petal shape.*—Rotund.
- *Petal margin.*—Entire.
- *Petal apex.*—Retuse.
- *Petal base.*—Cordate.
- *Petal surface.*—Glabrous.
- *Petal color.*—155B.
- *Calyx shape.*—Stellular.
- *Calyx diameter.*—1 cm.
- *Sepal number.*—3 in number.
- *Sepals fused or unfused.*—Unfused.
- *Sepal dimensions.*—4 mm. in length and 3 mm. in width.
- *Sepal shape.*—Ovate.
- *Sepal form.*—Petaloid.
- *Sepal apex.*—Apiculate.
- *Sepal base.*—Truncate.
- *Sepal surface.*—Glabrous.
- *Sepal color.*—155B, 160A, 187C.
- *Bud shape.*—Ovoid.
- *Bud dimensions.*—2.25 mm. in diameter and 3 mm. in length.
- *Bud color.*—155B, N144B, 160A 187C.
- *Bud surface.*—Glabrous.
- *Bud apex.*—Obtuse.

*Bud base.*—Truncate.
*Flower fragrance.*—None observed.
*Lastingness of flower.*—Range of 3–5 days.
*Flowering stem.*—Peduncle shape: Subterete. Peduncle surface: Glabrous. Peduncle color: 143A. Peduncle length: 20 cm. Peduncle width: 2 cm. Pedicel shape: Subterete. Pedicel surface: Glabrous. Pedicel color: 187C. Pedicel length: 1.25 cm. Pedicel width: 1 mm. Bract: Average of 4 per peduncle. Bract color: 143A. Bract dimensions: Average length 2.75 cm. and 0.60 cm. in width. Bract attachment: Sheathing. Bract shape: Ensiform and folded toward base. Bract margin: Entire. Bract apex: Epiculate. Bract base: truncate. Bract surface: Glabrous. Bract internode length: 1.50 cm.

Reproductive organs:
*Stamens.*—Three.
*Stamen color.*—155B.
*Stamen length.*—1 cm.
*Anther color.*—160C.
*Anther dimensions.*—1.50 mm. in length and 2.50 mm. in width.
*Amount of pollen.*—Minimal.
*Pollen color.*—160C.
*Pistil length.*—0.75 cm.
*Pistil color.*—155B.
*Stigma shape.*—Forked.
*Stigma height and diameter.*—3 mm.
*Stigma color.*—155B (white).
*Ovary color.*—N144B.
*Ovary surface.*—Glabrous.
*Ovary appearance.*—Glossy.
*Ovary shape.*—Subterete.
*Ovary dimensions.*—0.20 cm. in diameter and 0.60 cm. in height.
*Ovary position.*—Inferior.

Fruit and seed:
*Dimensions of fruit.*—10 mm to 15 mm in length; 7 mm to 10 mm in width.
*Shape of fruit.*—Barrel shaped capsule.
*Color of fruit.*—Mid green, ripens to yellow.
*Texture of fruit.*—Firm.
*Surface of fruit.*—Smooth with some pitting or depressions.
*Quantity of seeds per fruit.*—Ranges from 10 to 25.
*Dimensions of seed.*—1 mm in diameter.
*Shape of seed.*—Close to spherical.
*Color of seed.*—Bright orange.
*Surface of seed.*—Smooth.

It is claimed:

1. A new and distinct variety of *Libertia* plant named 'TAUPO BLAZE' as described and illustrated herein.

* * * * *